United States Patent [19]

Hammer et al.

[11] Patent Number: 4,567,210
[45] Date of Patent: Jan. 28, 1986

[54] PROCESS FOR FOAMING THERMOPLASTIC AROMATIC POLYCARBONATES

[75] Inventors: Heinz Hammer, Cologne; Klaus Kircher, Leverkusen; Rolf-Volker Meyer, Krefeld, all of Fed. Rep. of Germany

[73] Assignee: Bayer Aktiengesellschaft, Bayerwerk, Fed. Rep. of Germany

[21] Appl. No.: 697,996

[22] Filed: Feb. 4, 1985

[30] Foreign Application Priority Data

Feb. 15, 1984 [DE] Fed. Rep. of Germany ....... 3405418

[51] Int. Cl.$^4$ .................................................. C08J 9/10
[52] U.S. Cl. ......................................... 521/90; 521/95; 521/97; 521/180
[58] Field of Search ........................... 521/180, 90, 95

[56] References Cited

U.S. PATENT DOCUMENTS

| | | | |
|---|---|---|---|
| 3,554,932 | 1/1971 | Overcashier | 521/182 |
| 3,779,954 | 12/1973 | Wirth et al. | 260/2.5 |
| 4,065,401 | 12/1977 | Cohnen et al. | 252/350 |
| 4,097,425 | 6/1978 | Niznik | 521/180 |
| 4,110,273 | 8/1978 | Cohnen et al. | 521/59 |
| 4,163,037 | 7/1979 | Niznik | 264/54 |
| 4,174,432 | 11/1979 | Niznik | 521/128 |
| 4,263,409 | 4/1981 | Liberti | 521/81 |
| 4,288,560 | 9/1981 | Kirchmayr | 521/90 |
| 4,313,873 | 2/1982 | Lim | 260/18 |
| 4,500,653 | 2/1985 | Schmidt et al. | 521/182 |

FOREIGN PATENT DOCUMENTS 0007437 2/1979 European Pat. Off. .
0130447 6/1984 European Pat. Off. .

OTHER PUBLICATIONS

Kunststoffe 62 (10), 687 (1972).
Chem. Ber. 82, pp. 121–123 (1949).
Tetrahedron Letters (44), pp. 3875–3878 (1974).

*Primary Examiner*—Morton Foelak
*Attorney, Agent, or Firm*—Gene Harsh; Lawrence S. Pope; Aron Preis

[57] ABSTRACT

The present invention relates to a process for foaming thermoplastic aromatic polycarbonates, 2-phenyl-1-oxa-3,4-diazol-5-ones acylated in the 4-position being used in combination with cyanuric acid.

6 Claims, No Drawings

PROCESS FOR FOAMING THERMOPLASTIC AROMATIC POLYCARBONATES

Foaming of thermoplastic aromatic polycarbonates with blowing agents is known (see, for example, Kunststoffe 62 (10), 687 (1972)).

It is also known that a blowing agent combination can be used as the blowing agent (see, for example, DE-OS (German Published Specification) No. 2,441,418).

It is furthermore known that the processing temperature of polycarbonate can be reduced for the preparation of a blowing agent concentrate (see, for example, U.S. Pat. No. 4,313,873 and EP-OS (European Published Specification) No. 0,007,437).

The object of the present invention is thus to use a blowing agent system in the foaming of polycarbonates which does not cause too much degradation of carbonic acid ester bonds in the polycarbonate, and which, secondly, allows a relatively high incorporation temperature, so that polycarbonate granules which contain blowing agent and can be stored can be prepared, and which, thirdly, permits as low as possible a processing temperature during processing of the polycarbonate to foamed articles. A processing temperature of only at most 290° C.–300° C. is frequently possible for foaming polycarbonate. A blowing agent which can function adequately at this processing temperature must already have a sufficient rate of decomposition at a material temperature of 265° C.–275° C.

Taking into consideration a safety margin of at least 25° C. between this decomposition temperature and the preparation temperature of a blowing agent concentrate, such blowing agents are suitable at a maximum of 240° C.–250° C. for the preparation of blowing agent concentrates in the polycarbonate.

In order thus to be able to use a blowing agent which decomposes sufficiently only above 275° C., an additive is required which reduces the decomposition of the blowing agent and hence reduces the processing temperature of the blowing agent concentrates resulting in polycarbonate foams.

Surprisingly, a process has now been found for foaming aromatic thermoplastic polycarbonates which can be applied at processing temperatures of 270° C.–320° C., fulfils the desired requirements and is characterised in that compounds of the formula I

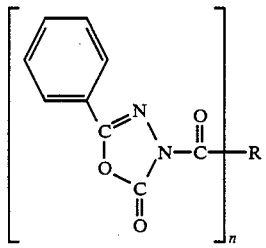 (I)

wherein
n=1 and
R denotes $C_1$–$C_{18}$-alkoxy, $C_6$–$C_{12}$-cycloalkoxy, $C_6$–$C_{18}$-aryl, $C_6$–$C_{12}$-aryloxy, $C_7$–$C_{18}$-aralkyl, $C_7$–$C_{18}$-aralkoxy, $C_7$–$C_{18}$-alkaryl or $C_7$–$C_{18}$-alkaryloxy,
or wherein
n=2 and
R denotes $C_6$–$C_{18}$-arylene, $C_6$–$C_{18}$-arylenedioxy, isopropylidene-bis-(phenylene-oxy) or $C_1$–$C_5$-alkylene, or is a single bond, and which must also have a decomposition temperature in bulk of at least 265° C., preferably of at least 275° C., are used as the blowing agents in amounts of 0.02 to 5% by weight, preferably 0.03 to 3% by weight and in particular 0.04 to 1% by weight, based on the weight of thermoplastic polycarbonate, together with cyanuric acid in amounts of 0.0005 to 2% by weight, preferably 0.0008–0.5% by weight, again based on the weight of thermoplastic polycarbonate.

According to U.S. Pat. No. 4,097,425 and 4,163,037, dihydrooxadiazinones are used as blowing agents for polycarbonates, and dioxazolones are used according to U.S. Pat. No. 4,288,560, and because of the composition properties of the dihydrooxadiazinones and dioxazolones differs from those of the blowing agents based on oxadiazolones of the formula I and used according to the invention, the present problem is not discussed in those patent specifications.

5-Phenyltetrazole (see, for example, U.S. Pat. No. 4,263,409) and benzazimides (U.S. Pat. No. 3,779,954) are also described as blowing agents for polycarbonates, and have the disadvantage that they have a relatively powerful adverse influence on molecular weight degradation of the polycarbonate during foaming.

The oxadiazolones of the formula I to be used according to the invention are either known or obtainable by known processes.

The preparation of the compounds which are already known is described in Chem. Ber. 82, pages 121–123 (1949) and in Tetrahedron Letters (44) pages 3875–3878 (1974). The other oxadiazolones of the formula I which have not previously been described and are to be used according to the invention can be prepared by processes analogous to those described in these literature references.

In detail, the compounds are synthesised by reacting benzoic acid hydrazides with phosgene in a suitable solvent, such as, for example, methylene chloride, chlorobenzene, toluene, xylene, water, acetone, chloroform, tetrachloroethane or mixtures thereof. The resulting 2-phenyl-1-oxa-3,4-diazol-5-one is then reacted with one equivalent of a monocarboxylic acid chloride or monochlorocarbonic acid ester, or with half an equivalent of a dicarboxylic acid chloride of dichlorocarbonic acid ester in the presence of an acid-trapping agent.

Suitable monocarboxylic acid chlorides and monochlorocarbonic acid esters are those of the formula II

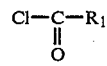 (II)

wherein
$R_1$ has the meaning of the monovalent radicals R from formula I;
suitable dicarboxylic acid chlorides and dichlorocarbonic acid esters are those of the formula III

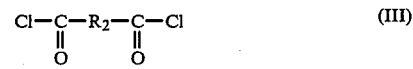 (III)

wherein
$R_2$ has the meaning of the divalent radicals R from formula I or is a single bond.

Particularly suitable carboxylic acid chlorides or chlorocarbonic acid esters of the formula II are benzoic acid chloride, naphthoic acid chloride and chlorocarbonic acid phenyl ester, ethyl ester and propyl ester.

Particularly suitable dicarboxylic acid dichlorides or dichlorocarbonic acid esters of the formula III are isophthalic acid dichloride, terephthalic acid dichloride, succinic acid dichloride, oxalic acid dichloride, malonic acid dichloride and the bis-chlorocarbonic acid esters of bisphenol A.

Tertiary amines, such as, for example, pyridine or triethylamine, or alkali metal hydroxides can be used as acid-trapping agents in the reaction of the 2-phenyloxadiazolone with the acid chloride.

Aromatic polycarbonates to be foamed according to the invention are polycondensates which are synthesised by reacting diphenols with phosgene or diesters of carbonic acid in a known manner.

Examples of suitable diphenols are hydroquinone, resorcinol, 4,4'-dihydroxydiphenyl, bis-(hydroxyphenyl)-alkanes, such as, for example, 2,2-bis-(4-hydroxyphenyl)-propane (bisphenol A), 2,2-bis-(4-hydroxy-3,5-dimethylphenyl)-propane (tetramethylbisphenol A), halogenated bis-(hydroxyphenyl)-alkanes, such as, for example, 2,2-bis-(4-hydroxy-3,5-dichlorophenyl)-propane (tetrachlorobisphenol A), and 2,2-bis-(4-hydroxy-3,5-dibromophenyl)-propane (tetrabromobisphenol A), trinuclear phenols, such as $\alpha,\alpha'$-bis-(4-hydroxyphenyl)-p-diisopropylbenzene, and bis-(hydroxyphenyl) sulphides, sulphoxides, sulphones or ethers.

Other diphenols which are suitable for the preparation of polycarbonate are described in U.S. Pat. Nos. 3,028,365, 2,999,835, 3,148,172 and 2,999,846.

The aromatic polycarbonates should as a rule have average weight-average molecular weights $\overline{M}_w$ of 10,000 to more than 200,000, preferably 20,000 to 80,000, determined by measurements of the relative solution viscosity in $CH_2Cl_2$ at 25° C. and at a concentration of 0.5 g in 100 ml of $CH_2Cl_2$.

The aromatic thermoplastic polycarbonates to be foamed according to the invention can be linear or branched.

The co-use, according to the invention, of cyanuric acid thus enables storable granules of blowing agents of the formula I to be prepared beforehand in thermoplastic polycarbonates in amounts of 1 to 20% by weight, preferably 5 to 10% by weight, at temperatures from 200° C. to 270° C. in the usual mixing units, such as single-screw extruders or twin-screw extruders or kneaders, in a known manner, it being possible for these granules to be processed as "concentrates", in each case together with further thermoplastic polycarbonate and the cyanuric acid according to the process according to the invention at temperatures of 270° C. to 320° C. on injection-moulding machines in a known manner to give polycarbonate foams.

The cyanuric acid can also be added in the form of mixtures in the polycarbonate, which can be prepared beforehand at the usual compounding temperatures for polycarbonates, contents of cyanuric acid in the polycarbonate of 0.0005 to 5% by weight, preferably 0.0008 to 2% by weight, being usual.

Such separate mixtures of cyanuric acid in the polycarbonate can now be used for the foaming process according to the invention either with further thermoplastic polycarbonate and the polycarbonate granules containing the blowing agent, or, if appropriate, only with the polycarbonate granules containing blowing agent, or, if appropriate, only with the blowing agent.

The foaming process according to the invention can, of course, also be carried out by using the blowing agent and/or the cyanuric acid in bulk, that is to say in undiluted form.

The components of blowing agent, cyanuric acid and thermoplastic polycarbonate to be used for carrying out the process according to the invention, if appropriate in the form of complete or partial separate mixtures of cyanuric acid and/or blowing agent with polycarbonate, are subjected to intimate physical mixing in the usual manner at room temperature before the processing to polycarbonate foam or polycarbonate foamed articles.

Certain amounts of up to 8% by weight, based on the weight of polycarbonate, of, for example, glass fibres or mineral fillers are advantageous as nucleating agents for the preparation of a particularly fine-cellular foam.

Apart from the blowing agents of the formula I to be used according to the invention, the cyanuric acid and the abovementioned glass fibres and fillers, the customary additives, such as heat and UV light stabilisers, flameproofing agents, pigments, dyestuffs or lubricants, and larger amounts of glass fibres and fillers can also be added to the polycarbonates.

The polycarbonates foamed by the process according to the invention can be used as shaped articles or foamed articles in all cases where polycarbonate foam has hitherto been used, thus, for example, for the production of large-area covers for lamps, housings and office equipment and for the production of large-area cupboard elements.

EXAMPLE 1

Preparation of di-[2-phenyl-1,3,4-oxadiazol-5-one]-4-terephthalamide 68 g (0.5 mole) of benzhydrazide are suspended in 500 ml of water/acetone, and 55-60 g (about 10-20 mole % excess) of phosgene are passed in at 10° C.-20° C. The pH value is kept at about 2 to 2.5 by simultaneous dropwise addition of 45% strength NaOH. The mixture is stirred at 20° C. for a further half an hour. The precipitate is filtered off with suction, washed with water and dried at 100° C. in vacuo. The resulting 2-phenyl-1,3,4-oxadiazol-5-one is introduced into 500 ml of toluene, 50 g (0.6 mole) of pyridine are added, and 51 g (0.25 mole) of terephthalic acid dichloride in 150 ml of toluene are added dropwise. The mixture is stirred at 25° C. for 45 minutes and then heated at the reflux temperature for another ½ hour.

After cooling, the mixture is poured into a relatively large amount of water and the precipitate is filtered off with suction and washed free with alcohol and water chloride-free. The precipitation is dried at 80°-100° C. in vacuo. The yield is 88 g=78% of theory. Melting point: 282° C., decomposition temperature: 285° C.

EXAMPLE 2

Splitting off of gas from various blowing agent mixtures as a function of the temperature was carried out in a standard device (flask, pneumatic trough). The heating up rate was 7.5° C./minute. The device is suitable for comparative investigations, and gives only relative and no absolute values.

The following were investigated:

Blowing agent 1: 2 g of di-(2-phenyl-1,3,4-oxadiazol-5-one)-4-terephthalamide

Blowing agent mixture 2: 2 g of blowing agent 1+0.02 g (=1%) of cyanuric acid

Blowing agent mixture 3: 2 g of blowing agent 1+0.1 (=5%) of cyanuric acid

Blowing agent mixture 4: 2 g of blowing agent 1+0.2 g (=10%) of cyanuric acid

TABLE 1

| °C. | Blowing agent 1 mL | Blowing agent mixtures 2 amount of gas | 3 | 4 |
|---|---|---|---|---|
| 200 | 0 | 0 | 0 | 0 |
| 205 | 4 | 14 | 13 | 9 |
| 210 | 7 | 15 | 14 | 12 |
| 215 | 8 | 16 | 15 | 13 |
| 220 | 9 | 16 | 16 | 13 |
| 225 | 10 | 17 | 16 | 14 |
| 230 | 10 | 18 | 17 | 15 |
| 235 | 12 | 18 | 18 | 15 |
| 240 | 12 | 19 | 19 | 17 |
| 245 | 13 | 20 | 20 | 18 |
| 250 | 14 | 22 | 22 | 20 |
| 255 | 15 | 25 | 25 | 23 |
| 260 | 18 | 28 | 30 | 29 |
| 265 | 21 | 33 | 40 | 42 |
| 270 | 26 | 42 | 60 | 60 |
| 275 | 34 | 57 | 83 | 83 |
| 280 | 45 | 73 | 108 | 110 |
| 285 | 60 | 90 | 135 | 138 |
| 290 | 80 | 107 | 160 | 162 |
| 295 | 104 | 127 | 184 | 195 |
| 300 | 124 | 150 | 204 | 222 |
| 305 | 145 | 171 | 222 | 241 |
| 310 | 163 | 190 | 237 | 254 |
| 315 | 180 | 207 | 246 | 264 |
| 320 | 198 | 220 | 254 | 271 |

EXAMPLE 3

5 g of cyanuric acid were introduced onto 5000 g of a bisphenol A homopolycarbonate with a relative solution viscosity of 1.313 in a fluidised bed mixer and the mixture was then compounded on a devolatilisation extruder, the individual heating zones being set as follows: 240° C. (intake zone), 230° C., 240° C., 240° C., 230° C., 230° C. and 220° C. (nozzle). The extruded melt issuing from the extruder was cut to granules; the resulting granules were almost completely transparent and had a relative solution viscosity of 1.307. The drop in relative solution viscosity from 1.313 to 1.307 over a single compounding step indicates that the cyanuric acid has no noticeable influence on the molecular weight degradation of the polycarbonate, since such a decrease in the solution viscosity can also occur on extrusion of the polycarbonate without the use of cyanuric acid.

EXAMPLE 4

The polycarbonate granules described in Example 3 containing 0.1% by weight of cyanuric acid, based on the weight of polycarbonate, were processed, after predrying, to test pieces of dimensions 60 mm×6 mm×4 mm at a material temperature of 290° C. on an Anker injection-moulding machine.

The relative solution viscosity of the polycarbonate measured on the test piece was 1.304. A drop in relative solution viscosity from 1.307 to 1.304 has thus taken place under this exposure to heat and mechanical stress, and this can be regarded as a typical degradation of polycarbonate in the injection-moulding process. No additional molecular weight degradation thus occurs here as a consequence of the presence of 0.1% by weight of cyanuric acid.

EXAMPLE 5

100 g of bisphenol A homopolycarbonate (relative solution viscosity 1.310) containing 5% by weight of glass fibres, based on the polycarbonate+glass fibres, (density of the polycarbonate containing glass fibres=1.24 g/cm$^3$) were (a) mixed with 10 g of a bisphenol A homopolycarbonate (relative solution viscosity 1,290), containing 5% by weight of incorporated blowing agent of Example 1, and (b) mixed with 10 g of polycarbonate, containing cyanuric acid, from Example 3 (relative solution viscosity 1.307), and the components were mixed thoroughly with one another and, after pre-drying, were processed to circular plates (200 mm in diameter, 8 mm thick, density: 0.9 g/cm$^3$) on an Anker injection-moulding machine at a temperature profile of 250° C. (intake zone), 300° C., 300° C., 300° C. (nozzle) in a water-cooled mould. The polycarbonate of the circular plates has a relative solution viscosity of 1.274.

The total cycle time was 1.5 minutes. Moulded articles with a uniform, fine-cellular structure and a good surface resulted; the cavity of the mould was filled completely.

EXAMPLE 6 (comparison example)

Example 5 was repeated, but without the co-use of the polycarbonate containing cyanuric acid.

The polycarbonate of the circular plates had a relative solution viscosity of 1.275. The total cycle time was 1.5 minutes. The resulting moulded articles did not completely fill the cavity of the mould, and in particular clear sites of collapse occurred at the flow end as the result of an inadequate blowing action.

EXAMPLE 7 (comparison example)

Bisphenol A homopolycarbonate (relative solution viscosity 1.310) containing 5% by weight of glass fibres, based on the polycarbonate+glass fibres, was mixed with 0.4% by weight, based on the polycarbonate containing glass fibres, of 5-phenyltetrazole in an eccentric tumbling mixer and the mixture was then injection-moulded to circular plates of dimensions 200 mm×8 mm with a density of 0.9 g/cm$^3$ at a temperature profile of the plasticising unit of 200° C. (intake zone), 250° C., 280° C., 300° C., 300° C. (nozzle). The polycarbonate of the circular sheets has a relative solution viscosity of 1.251.

EXAMPLE 8 (comparison example)

Example 7 is repeated, 0.5% by weight, based on the polycarbonate containing glass fibres, of the blowing agent of Example 1 being used in the mixture instead of 0.4% by weight of 5-phenyltetrazole. The injection moulding to circular plates (200 mm×8 mm) with a density of 0.9 g/cm$^3$ subsequently has to be carried out at a temperature profile of the plasticising unit of 200° C. (intake zone), 250° C., 300° C., 320° C., 320° C. (nozzle), in order to achieve adequate filling of the cavity of the mould and moulded articles without sites of collapse. The polycarbonate of the circular sheets had a relative solution viscosity of 1.264. In spite of the higher processing temperature required, the degradation of the polycarbonate is less than in Example 7.

We claim:

1. A process for foaming an aromatic thermoplastic polycarbonate at a temperature from 270° C. to 320° C., which also contains, if desired, a nucleating agent, in which a compound of the general formula

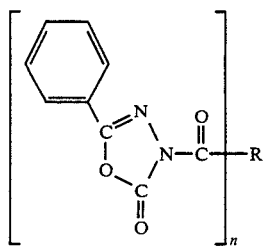

wherein
n is 1 and
R denotes $C_1$–$C_{18}$-alkoxy, $C_6$–$C_{12}$-cycloalkoxy, $C_6$–$C_{18}$-aryl, $C_6$–$C_{12}$-aryloxy, $C_7$–$C_{18}$-aralkyl, $C_7$–$C_{18}$-aralkoxy, $C_7$–$C_{18}$-alkaryl or $C_7$–$C_{18}$-alkaryloxy,
or wherein
n is 2 and
R denotes $C_6$–$C_{18}$-arylene, $C_6$–$C_{18}$-arylene dioxy, isopropylidene-bis-(phenylene-oxy) or $C_1$–$C_5$-alkylene,
or wherein
n is 2 and
R is a single bond,
and which must also have a decomposition temperature in bulk of at least 265° C., is used, in an amount of 0.02 to 5% by weight, based on the weight of thermoplastic polycarbonate, as a blowing agent in the presence of cyanuric acid in an amount of 0.0005 to 2% by weight, again based on the weight of thermoplastic polycarbonate.

2. A process according to claim 1, in which the compound of the formula (I) is used in an amount of 0.03 to 3% by weight.

3. A process according to claim 2, in which the compound of formula (I) is used in an amount of 0.04 to 1% by weight.

4. A process according to claim 1, in which a compound of formula (I) having a decomposition temperature of at least 275° C. is used.

5. A process according to claim 1, in which the compound of formula (I) is the reaction product of 2-phenyl-1-oxa-3,4-diazol-5-one with one equivalent of benzoic acid chloride, naphthoic acid chloride or chlorocarbonic acid phenyl ester, -ethyl ester or -propyl ester, or with half an equivalent of isophthalic acid dichloride, terephthalic acid dichloride, succinic acid dichloride, oxalic acid dichloride, malonic acid dichloride or the bis-chlorocarbonic acid esters of bisphenol A.

6. A process according to claim 1, in which cyanuric acid is used in amounts of 0.0008 to 0.5% by weight.

* * * * *